(12) United States Patent
Liu et al.

(10) Patent No.: US 9,458,140 B2
(45) Date of Patent: Oct. 4, 2016

(54) FURANONE COMPOUNDS AS KINASE INHIBITORS

(71) Applicant: Eternity Bioscience Inc., Cranbury, NJ (US)

(72) Inventors: Dong Liu, Bridgewater, NJ (US); Minsheng Zhang, Warren, NJ (US)

(73) Assignee: Eternity Bioscience Inc., Cranbury, NJ (US)

( * ) Notice: Subject to any disclaimer, the term of this patent is extended or adjusted under 35 U.S.C. 154(b) by 0 days.

(21) Appl. No.: 14/889,507

(22) PCT Filed: May 8, 2014

(86) PCT No.: PCT/US2014/037247
§ 371 (c)(1),
(2) Date: Nov. 6, 2015

(87) PCT Pub. No.: WO2014/182873
PCT Pub. Date: Nov. 13, 2014

(65) Prior Publication Data
US 2016/0096825 A1    Apr. 7, 2016

Related U.S. Application Data

(60) Provisional application No. 61/820,853, filed on May 8, 2013.

(51) Int. Cl.
| | | |
|---|---|---|
| A61K 31/506 | (2006.01) | |
| C07D 405/04 | (2006.01) | |
| C07D 405/14 | (2006.01) | |
| C07D 417/14 | (2006.01) | |
| A61K 31/53 | (2006.01) | |
| A61K 31/443 | (2006.01) | |
| A61K 31/444 | (2006.01) | |

(52) U.S. Cl.
CPC ........... *C07D 405/04* (2013.01); *C07D 405/14* (2013.01); *C07D 417/14* (2013.01); *A61K 31/443* (2013.01); *A61K 31/444* (2013.01); *A61K 31/506* (2013.01); *A61K 31/53* (2013.01)

(58) Field of Classification Search
CPC   C07D 405/14; C07D 417/14; C07D 405/04; A61K 31/53; A61K 31/506; A61K 31/443; A61K 31/444
See application file for complete search history.

(56) References Cited

U.S. PATENT DOCUMENTS

| | | | | |
|---|---|---|---|---|
| 4,606,756 A * | 8/1986 | Ward | ..................... | A01N 43/36 504/248 |
| 5,889,027 A * | 3/1999 | Lee | ....................... | C07D 405/04 514/336 |
| 6,492,416 B1 * | 12/2002 | Shin | ..................... | C07D 307/58 514/256 |
| 8,071,595 B2 * | 12/2011 | Ripka | .................. | C07D 401/04 514/241 |
| 8,343,973 B2 * | 1/2013 | Ripka | .................. | C07D 487/04 514/248 |
| 2010/0105714 A1 * | 4/2010 | Sun | ....................... | C07D 405/04 514/278 |
| 2010/0137317 A1 * | 6/2010 | Ripka | .................. | C07D 401/04 514/241 |
| 2010/0292238 A1 * | 11/2010 | Ripka | .................. | C07D 487/04 514/248 |
| 2011/0172215 A1 | 7/2011 | Adjabeng et al. | | |
| 2016/0002250 A1 * | 1/2016 | Oliver | .................. | C07D 487/04 514/248 |

FOREIGN PATENT DOCUMENTS

| | | | |
|---|---|---|---|
| EP | 0822190 A1 | 2/1998 | |
| KR | WO 0061571 A1 * | 10/2000 | ........... C07D 307/58 |

OTHER PUBLICATIONS

J. Tsai et al., 105 PNAS 3041-3046 (2008).*
S. H. Lee et al., 22 Oncogene, 6942-6945 (2003).*
Leung et al., Liver International, 1315-1323 (2010).*
F. Selcukbircik et al., 18 JBUON, 116-123 (2012).*
N. Ishimura et al., 199 Cancer Letters, 169-173 (2008).*
D. Bell, 18 Modern Pathology, 519-532 (2005).*

* cited by examiner

*Primary Examiner* — Alexander R Pagano
(74) *Attorney, Agent, or Firm* — Fox Rothschild LLP; Wansheng Jerry Liu

(57) ABSTRACT

The present disclosure provides novel furanone compounds, or pharmaceutically acceptable salts, solvates or prodrugs thereof, as Raf kinase, especially BRAF kinase, inhibitors, which are useful therapeutic agents for treatment of Raf kinase related diseases or disorders, such as melanomas, cancers, and leukemia. The disclosure also provides methods and processes for preparing these novel furanone compounds, pharmaceutical compositions containing these furanone compounds, and methods of treatment using these furanone compounds.

31 Claims, No Drawings

FURANONE COMPOUNDS AS KINASE INHIBITORS

CROSS-REFERENCE TO RELATED APPLICATIONS

This application is a U.S. national phase application of International Application No. PCT/US2014/037247, filed on May 8, 2014, which in turn claims priority to U.S. Provisional Application No. 61/820,853, filed on May 8, 2013. The disclosures of both applications are incorporated herein by reference in their entireties.

FIELD OF THE INVENTION

The present invention relates to novel furanone compounds, and compositions thereof, useful as kinase inhibitors useful for the treatment of hyperproliferative diseases, such as various cancers, melanomas and leukemia.

BACKGROUND OF THE INVENTION

Kinases are a superfamily of enzymes that transfer a phosphate group from ATP to target proteins. There are more than 518 kinases encoded in the human genome, including 90 tyrosine kinases, 388 serine/threonine kinases and 40 atypical kinases (Manning, G., et al., *Science*, 2002, 298 (5600): 1912-1934). They play vital roles in cell activation, proliferation, differentiation, migration, vascular permeability, and so on. Dysfunction of kinases has been implicated in various diseases such as cancer, inflammation, cardiovascular diseases, diabetes, and neuronal disorders. Several kinase inhibitors have been developed for the treatment of cancers, including but not limited to imatinib, dasatinib, nilotinib, gefitinib, erlotinib, lapatinib, sunitinib, sorafenib, pazopanib, evrolimus, trastuzumab, cetuximab, panitumumab, and bevacizumab (Knight, Z. A., et al., *Nat. Rev. Cancer*, 2010, 10(2): 130-137).

BRAF is a member of the Raf kinase family of serine/threonine-specific protein kinases. BRAF plays an important role in regulating the MAPK/ERK signaling pathway, which affects cell division, proliferation, differentiation, and secretion. The RAS/RAF/MEK/ERK pathway acts as a signal transducer to send extracellular signals such as hormones, cytokines, and various growth factors into cell nucleus, directing a range of biochemical and physiological processes including cell differentiation, proliferation, growth, and apoptosis (McCubrey, J. A., et al., *Biochim. Biophys. Acta*, 2007, 1773 (8): 1263-84). The RAS/RAF/MEK/ERK pathway is frequently mutated in many human cancers (Downward, J., *Nat. Rev. Cancer*, 2003, 3 (1): 11-22). The finding that mutations in BRAF caused a wide range of human cancers and many of these tumors are dependent on the constitutive activation of BRAF/MEK/ERK pathway fueled drug discovery efforts in searching for small molecule inhibitors targeting BRAF mutants (especially the most common form of BRAF$^{V600E}$) (Davies, H., et al., *Nature*, 2002, 417: 949-954) (Flaherty, K. T., et al., *New Engl. J. Med.*, 2010, 363: 809-819). It was found that BRAF mutations are responsible for more than 50% of malignant melanomas, ~45% of papillary thyroid cancer, 10% of colorectal cancers, and had also been identified in ovarian, breast, and lung cancers (Cantwell-Dorris, E. R., et al., *Molecular Cancer Therapy*, 2011, 10: 385-394). Recently it was reported that almost all hairy-cell leukemia patients carry BRAF$^{V600E}$ mutation and inhibition of the enzyme caused significant remission of the disease (Sascha, D., et al., *New Engl. J. Med.*, 2012, 366:2038-2040). BRAF-specific inhibitors such as Vemurafenib (RG7204), PLX-4720, GDC-0879, and Dabrofenib (GSK2118436) have been reported to be efficacious in causing tumor regression in both preclinical and clinical studies (Flaherty, K. T., et al., *New Engl. J. Med.*, 2010, 363: 809-819; Kefford, R. A., et al., *J. Clin. Oncol.*, 2010, 28: 15s).

Accordingly, the identification and development of small-molecules that specifically modulate BRAF$^{V600E}$ kinase activity will serve as therapeutic approaches for successful treatment of a variety of BRAF$^{V600E}$ kinase-related diseases or disorders, such as cancers.

SUMMARY OF THE INVENTION

The present invention provides novel furanone compounds as useful therapeutic agents for the treatment of diseases or disorders associated with kinase activities, especially hyperproliferative diseases or disorder associated with BRAF$^{V600E}$ kinase activity, for example, melanomas, cancers, and leukemia.

In one aspect, the present disclosure provides compounds of formula (I):

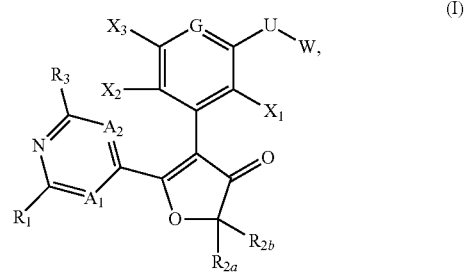

or a pharmaceutically acceptable salt, solvate (in particular hydrate), or prodrug thereof, wherein:

$A_1$ and $A_2$ are independently selected from CH and N;

G is N or $CX_4$;

$R_1$ is selected from hydrogen, halogen, $NR_{11}R_{14}$, $OR_{12}$, and $S(O)_{0-2}R_{13}$;

$R_{11}$ is selected from hydrogen, alkyl, alkenyl, alkynyl, cycloalkyl, cycloalkenyl, heterocyclyl, aryl, and heteroaryl, each group except hydrogen optionally substituted;

$R_{12}$, $R_{13}$, and $R_{14}$ are independently selected from hydrogen, alkyl and cycloalkyl;

$R_{2a}$ and $R_{2b}$ are independently selected from the group consisting of hydrogen, alkyl, alkenyl, alkynyl, cycloalkyl, cycloalkenyl, heterocyclyl, aryl, and heteroaryl; or $R_{2a}$ and $R_{2b}$ together with the carbon atom to which they are attached form a cyclic moiety selected from the group consisting of cycloalkyl, cycloalkenyl, and heterocyclyl, each optionally substituted;

$R_3$ is selected from hydrogen, halogen, hydroxyl, alkyl, alkoxy, and $NR_{31}R_{32}$;

$R_{31}$ and $R_{32}$ are independently selected from hydrogen and alkyl;

$X_1$ through $X_4$ are independently selected from hydrogen, halogen, cyano, nitro, hydroxyl, alkyl, alkoxy, and amino;

U is selected from —NH—, —NHC(O)—, NHS(O)$_n$—, NHC(O)O—, NHC(O)NH—, —O—, —C(O)—, —C(O)O—, —OC(O)NH—, —C(O)NH—, —S—, —SO$_2$—, and —S(O)$_n$NH—, wherein each n is independently 1 or 2; and W is selected from alkyl, alkenyl, alkynyl, cycloalkyl, cycloalkenyl, heterocyclyl, aryl, and heteroaryl; each optionally substituted. In another aspect, the present invention provides pharmaceutical compositions containing any of these novel compounds, or a pharmaceutically acceptable salt, solvate or prodrug thereof, and a pharmaceutically acceptable carrier.

In another aspect, the present invention provides methods of treating a hyperproliferative disease or disorder in a subject, the method comprising administering to the subject a therapeutically effective amount of any compound of the present invention, or a pharmaceutically acceptable salt, solvate or prodrug thereof. The compound of present invention is typically administered to a patient in a pharmaceutical formulation or dosage form that contains at least one pharmaceutically acceptable carrier.

In another aspect, the present invention provides use of the novel furanone compounds, or pharmaceutically acceptable salt, solvate or prodrugs thereof, in the manufacture of medicaments for treatment of a disease or disorder associated with a kinase activity.

Other aspects and embodiments of the present invention will be better appreciated through the following description, examples, and claims.

DETAILED DESCRIPTION OF THE INVENTION

In one embodiment, the present disclosure provides compounds of formula (II):

(II)

or a pharmaceutically acceptable salt, solvate or prodrug thereof, wherein $R_1$, $R_{2a}$, $R_{2b}$, $X_{1-3}$, G, U, W are as defined in formula I.

In another embodiment, the present disclosure provides a compound of formula (III):

(III)

or a pharmaceutically acceptable salt, solvate or prodrug thereof, wherein:

$R_{2a}$, $R_{2b}$, and $X_1$ through $X_4$ are as defined in formula I;

$R_{11}$ is selected from hydrogen, alkyl optionally substituted by 1 to 3 groups independently selected from alkyl, aryl, heteroaryl, cyano, cycloalkyl, heterocyclyl, halogen, hydroxyl, $NR_{15}R_{16}$, $OR_{17}$, and $S(O)_{0-2}R_{18}$;

$R_{15}$ is selected from hydrogen and optionally substituted alkyl, $C(O)R_{19}$, and $C(O)OR_{19}$;

$R_{16}$ is selected from hydrogen and optionally substituted alkyl;

$R_{17}$ is selected from alkyl, $C(O)R_{20}$, $C(O)NHR_{20}$;

$R_{18}$ is selected from alkyl, alkoxy, halogen, and hydroxyl;

$R_{19}$ is optionally substituted alkyl;

$R_{20}$ is selected from hydrogen and optionally substituted alkyl; and

W is selected from alkyl optionally substituted by 1 to 3 groups independently selected from hydroxyl, halogen, cyano, alkyl, alkoxy; and aryl optional substituted by 1 to 3 groups independently selected from hydroxyl, halogen, cyano, alkyl, alkoxy, amino, and nitro.

In another embodiment, the present invention relates to a compound of formula (IV):

(IV)

or a pharmaceutically acceptable salt, solvate, or prodrug thereof, wherein:

$R_{2a}$ and $R_{2b}$ are independently selected from the group consisting of hydrogen, alkyl, alkenyl, alkynyl, cycloalkyl, cycloalkenyl, heterocyclyl, aryl, and heteroaryl; or $R_{2a}$ and $R_{2b}$ together with the carbon atom to which they are attached, form a cyclic moiety selected from the group consisting of cycloalkyl, cycloalkenyl, and heterocyclyl;

$R_{11}$ is selected from hydrogen, alkyl optionally substituted by 1 to 3 groups independently selected from alkyl, aryl, heteroaryl, cyano, cycloalkyl, heterocyclyl, halogen, hydroxyl, $NR_{15}R_{16}$, $OR_{17}$, and $S(O)_{0-2}R_{18}$; wherein:

$R_{15}$ is selected from hydrogen and optionally substituted alkyl and $C(O)OR_{19}$, $R_{16}$ is selected from hydrogen and optionally substituted alkyl;

$R_{17}$ is selected from alkyl, $C(O)R_{20}$, and $C(O)NHR_{20}$;

$R_{18}$ is selected from alkyl, alkoxy, halogen and hydroxyl;

$R_{19}$ is optionally substituted alkyl;

$R_{20}$ is selected from hydrogen and optionally substituted alkyl;

$X_1$ through $X_4$ are independently selected from hydrogen, halogen, cyano, nitro, hydroxyl, alkyl, alkoxy, and amino; and $Y_1$ through $Y_5$ are independently selected from hydrogen, halogen, cyano, nitro, hydroxyl, alkyl, alkoxy, and amino.

In one preferred embodiment, $X_2$ and $X_4$ are hydrogen, and $X_1$ and $X_3$ are independently selected from fluorine (F) and chlorine (Cl).

In another preferred embodiment, $Y_1$ through $Y_5$ are independently selected from hydrogen and halogen; no more than two of $Y_1$ through $Y_5$ are halogens.

In another preferred embodiment, $R_{2a}$ and $R_{2b}$ are optionally substituted alkyl, or $R_{2a}$ and $R_{2b}$ together with the carbon atom to which they are attached form a cyclic moiety selected from the group consisting of cycloalkyl and heterocyclyl, each optionally substituted.

Yet other aspects and embodiments may be found in the description provided herein.

Pharmaceutical compositions or formulations of the present invention include those suitable for oral, nasal, topical (including buccal and sublingual), rectal, vaginal and/or parenteral administration. Regardless of the route of administration selected, the active ingredient(s) are formulated into pharmaceutically acceptable dosage forms by methods known to those of skill in the art.

The amount of the active ingredient(s) which will be combined with a carrier material to produce a single dosage form will vary depending upon the host being treated, the particular mode of administration and all of the other factors described above. The amount of the active ingredient(s) which will be combined with a carrier material to produce a single dosage form will generally be that amount of the active ingredient(s) which is the lowest dose effective to produce a therapeutic effect.

Methods of preparing pharmaceutical formulations or compositions include the step of bringing the active ingredient(s) into association with the carrier and, optionally, one or more accessory ingredients. In general, the formulations are prepared by uniformly mixing the active ingredient(s) into liquid carriers, or finely divided solid carriers, or both, and then, if necessary, shaping the product.

Exemplary, non-limiting examples of formulations of the invention suitable for oral administration may be in the form of capsules, cachets, pills, tablets, lozenges (using a flavored basis, usually sucrose and acacia or tragacanth), powders, granules, or as a solution or a suspension in an aqueous or nonaqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of the active ingredient(s).

In solid dosage forms of the invention for oral administration (capsules, tablets, pills, dragees, powders, granules and the like), the prodrug(s), active ingredient(s) (in their micronized form) is/are mixed with one or more pharmaceutically-acceptable carriers known to those of skill in the art. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof. Proper fluidity can be maintained, for example, by the use of coating materials, such as lecithin, by the maintenance of the required particle size, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monostearate and gelatin.

In some cases, in order to prolong the effect of the active ingredient(s), it is desirable to slow the absorption of the drug from subcutaneous or intramuscular injection. This may be accomplished by the use of a liquid suspension of crystalline or amorphous material having poor water solubility. The rate of absorption of the active ingredient(s) then depends upon its/their rate of dissolution which, in turn, may depend upon crystal size and crystalline form.

The formulations may be presented in unit-dose or multi-dose sealed containers, for example, ampoules and vials, and may be stored in a lyophilized condition requiring only the addition of the sterile liquid carrier, for example water for injection, immediately prior to use. Extemporaneous injection solutions and suspensions maybe prepared from sterile powders, granules and tablets of the type described above.

Any terms in the present application, unless specifically defined, will take the ordinary meanings as understood by a person of ordinary skill in the art.

As used herein, the singular forms "a", "an", and "the" include plural reference unless the context clearly dictates otherwise.

Unless stated otherwise, all aryl, cycloalkyl, heteroaryl, and heterocyclyl groups of the present disclosure may be substituted as described in each of their respective definitions. For example, the aryl part of an arylalkyl group, such as benzyl, may be substituted as described in the definition of the term "aryl."

The term "alkoxy," as used herein, refers to a $C_1$-$C_{10}$, preferably $C_1$-$C_6$, alkyl group attached to the parent molecular moiety through an oxygen atom. Representative examples of alkoxy group include, but are not limited to, methoxy ($CH_3O$—), ethoxy ($CH_3CH_2O$—), and t-butoxy (($CH_3$)$_3$CO—).

The term "alkyl," as used herein, refers to a group derived from a straight or branched chain saturated hydrocarbon by removal of a hydrogen from one of the saturated carbons. The alkyl group preferably contains from one to ten carbon atoms, more preferably one to six carbon atoms. Representative examples of alkyl group include, but are not limited to, methyl, ethyl, isopropyl, and tert-butyl.

The term "aryl," as used herein, refers to a group derived from a $C_6$-$C_{12}$, preferably $C_6$-$C_{10}$, aromatic carbocycle by removal of a hydrogen atom from an aromatic ring. The aryl group can be monocyclic, bicyclic or polycyclic. Preferred examples of aryl groups include phenyl and naphthyl.

The term "cyano," as used herein, refers to —CN.

The term "cycloalkyl," as used herein, refers to a group derived from a monocyclic saturated carbocycle, having preferably three to eight, more preferably three to six, carbon atoms, by removal of a hydrogen atom from the saturated carbocycle. Representative examples of cycloalkyl groups include, but are not limited to, cyclopropyl, cyclopentyl, and cyclohexyl. When a cycloalkyl group contains one or more double bond(s) in the ring, yet not aromatic, it forms a "cycloalkenyl" group.

The terms "halo" and "halogen," as used herein, refer to F, Cl, Br, or I.

The term "haloalkoxy," as used herein, refers to a $C_1$-$C_6$, preferably $C_1$-$C_4$, haloalkyl group attached to the parent molecular moiety through an oxygen atom.

The term "haloalkyl," as used herein, refers to a $C_1$-$C_{10}$, preferably $C_1$-$C_6$, more preferably $C_1$-$C_4$, alkyl group substituted by at least one halogen atom. The haloalkyl group can be an alkyl group of which all hydrogen atoms are substituted by halogens. Representative examples of haloalkyl include, but are not limited to, trifluoromethyl (CF$_3$—), 1-chloroethyl (ClCH$_2$CH$_2$—), and 2,2,2-trifluoroethyl (CF$_3$CH$_2$—).

The term "heteroaryl," as used herein, refers to a 5- to 10-membered, monocyclic or bicyclic aromatic group comprising one or more, preferably one to three, heteroatoms independently selected from nitrogen, oxygen, and sulfur in the aromatic ring(s). As is well known to those skilled in the art, heteroaryl rings have less aromatic character than their all-carbon counterparts. Thus, for the purposes of the invention, a heteroaryl group need only have some degree of aromatic character. Illustrative examples of heteroaryl groups include, but are not limited to, pyridyl, pyridazinyl, pyrimidyl, pyrazyl, triazinyl, pyrrolyl, pyrazolyl, imidazolyl, pyrimidinyl, furyl, thienyl, isoxazolyl, thiazolyl, isoxazolyl, oxazolyl, indolyl, quinolinyl, isoquinolinyl, benzisoxazolyl, benzothiazolyl, and benzothienyl.

The term "heterocyclyl," as used herein, refers to a 3- to 10-membered monocyclic or bicyclic nonaromatic group comprising one or more, preferably one to three, heteroatoms independently selected from nitrogen, oxygen, and sulfur in the nonaromatic ring(s). The heterocyclyl groups of the present disclosure can be attached to the parent molecular moiety through a carbon atom or a nitrogen atom in the group. A heterocylcyl group can be saturated or unsaturated, for example, containing one or more double bond(s) in the ring. Examples of heterocyclyl groups include, but are not limited to, morpholinyl, oxazolidinyl, piperazinyl, piperidinyl, pyrrolidinyl, tetrahydrofuryl, thiomorpholinyl, and indolinyl, or the like.

The terms "hydroxy" or "hydroxyl," as used herein, refers to —OH.

The term "nitro," as used herein, refers to —NO$_2$.

The term "oxo," as used herein, refers to "=O".

When any group, for example, alkyl, alkenyl, "cycloalkyl," "aryl," "heterocyclyl," or "heteroaryl", is said to be "optionally substituted," unless specifically defined, it means that the group is or is not substituted by from one to five, preferably one to three, substituents independently selected from halogen, alkyl, alkoxy, haloalkyl, haloalkoxy, hydroxy, oxo, acyl, cyano, nitro, and amino group, or the like, provided that such substitution would not violate the conventional bonding principles known to a person of ordinary skill in the art. When the phrase "optionally substituted" is used before a list of groups, it means that each one of the groups listed may be optionally substituted.

The compounds of the present disclosure can exist as pharmaceutically acceptable salts or solvates. The term "pharmaceutically acceptable salt," as used herein, means any non-toxic salt that, upon administration to a recipient, is capable of providing the compounds or the prodrugs of a compound of this invention. The salts can be prepared during the final isolation and purification of the compounds or separately by reacting a suitable nitrogen atom with a suitable acid. Acids commonly employed to form pharmaceutically acceptable salts include inorganic acids such as hydrochloric acid, hydrobromic acid, hydroiodic acid, sulfuric acid, phosphoric acid, hydrogen bisulfide as well as organic acids, such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid, acetic acid, and related inorganic and organic acids.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include, but are not limited to, lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, and N-methylmorpholine.

The term "solvate," as used herein, means a physical association of a compound of this invention with one or more, preferably one to three, solvent molecules, whether organic or inorganic. This physical association includes hydrogen bonding. In certain instances the solvate will be capable of isolation, for example when one or more, preferably one to three, solvent molecules are incorporated in the crystal lattice of the crystalline solid. Exemplary solvates include, but are not limited to, hydrates, ethanolates, methanolates, and isopropanolates. Methods of solvation are generally known in the art.

The term "therapeutically effective amount," as used herein, refers to the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially, or simultaneously.

The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

The term "patient" includes both human and other mammals.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

Synthetic Methods

The compounds and processes of the present invention will be better understood in connection with the following synthetic schemes that illustrate the methods by which the compounds of the invention may be prepared. Other reaction schemes could be readily devised by those skilled in the art based on the present disclosure.

Scheme 1

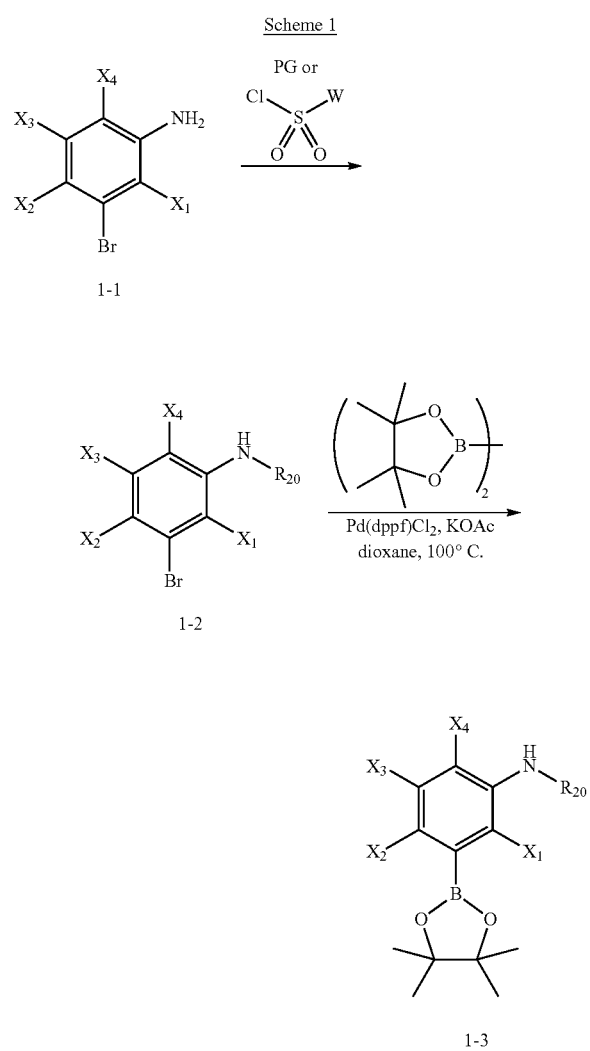

Amine 1-1 was purchased or prepared according to literature procedures. It was treated with sulfonyl chloride or protected by protecting group (Boc, Cbz, etc) to give 1-2. Bromide 1-2 was converted to corresponding boronic ester 1-3 via standard conditions (Scheme 1).

Scheme 2

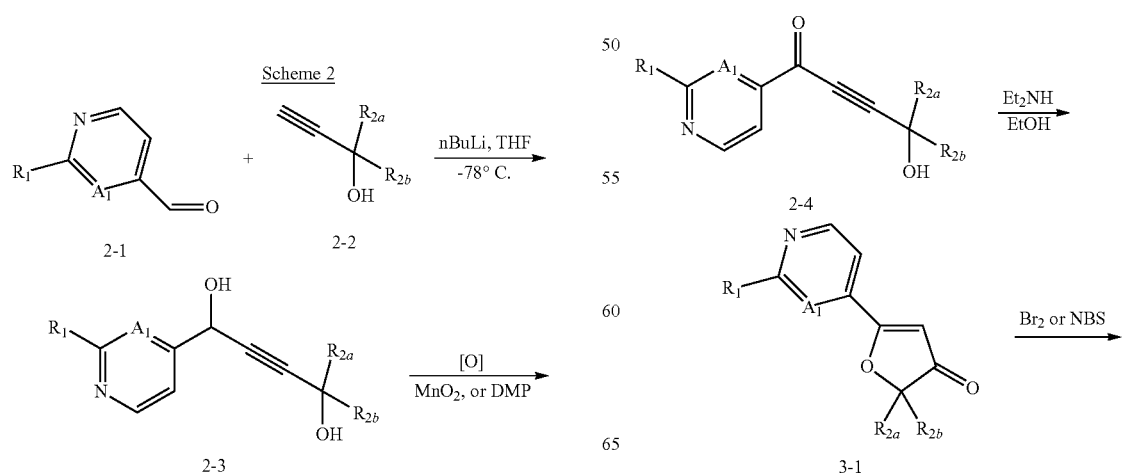

Aldehyde 2-1 reacted with lithiated propynol 2-2 to afford alcohol 2-3. Oxidation of 2-3 with $MnO_2$ or Dess-Martin periodinane gave ketone 2-4 (Scheme 2).

Alternately, protected propynol 2-6 was treated with nBuLi (or other strong bases), then reacted with methoxymethyl amide 2-5 to afford ketone 2-7, which upon deprotection gave 2-4 (Scheme 2).

Scheme 3

-continued

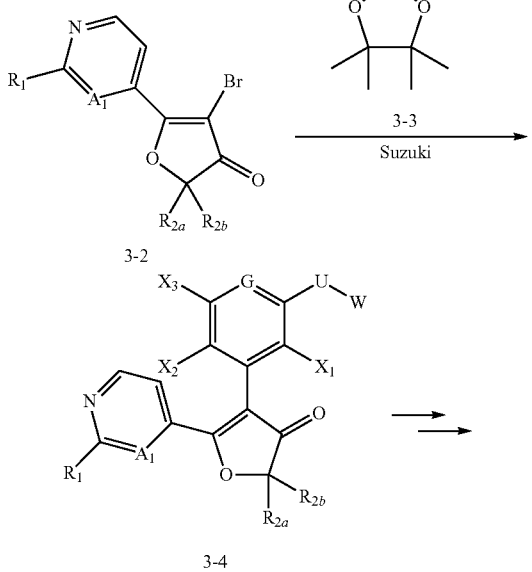

Alcohol 2-4 was treated with Et₂NH to afford cyclized product 3-1. Bromination with NBS or Br₂ gave bromide 3-2, which reacted with bronic ester 3-3 under Suzuki reaction conditions to give 3-4. Further modifications of $R_1$ and/or U-W gave 3-5.

Abbreviations

The abbreviations used in the descriptions of the schemes and the examples that follow are:
DCM for dichloromethane;
DIEA or DIPEA for diisopropyl ethylamine;
DMAP for N,N-dimethylaminopyridine;
DME for ethylene glycol dimethyl ether;
DMF for N,N-dimethyl formamide;
DMP for Dess-Martin periodinane;
DMSO for dimethylsulfoxide;
EDCI or EDC for 1-(3-diethylaminopropyl)-3-ethylcarbodiimide hydrochloride;
ESI for electrospray ionization;
Et for ethyl;
EtOAc for ethyl acetate;
g for gram(s);
h for hour(s);
HATU for O-(7-Azabenzotriazole-1-yl)-N,N,N',N'-tetramethyluronium hexafluoro-phosphate;
HBTU for O-Benzotriazole-N,N,N',N'-tetramethyl-uronium-hexafluoro-phosphate;
HPLC for high-performance liquid chromatography;
mCPBA for 3-Chloroperbenzoic acid;
Me for methyl;
MeOH for methanol;
mg for milligram(s);
min for minute(s);
MS for mass spectrometry;
NBS for N-Bromosuccinimide
NMR for nuclear magnetic resonance;
Pd(dppf)Cl₂ for [1,1'-Bis(diphenylphosphino)ferrocene]dichloropalladium(II);
PG for protecting groups;
Ph for phenyl;
PPh₃ for triphenylphosphine;
PTSA for p-Toluenesulfonic acid monohydrate
rt for room temperature;
TEA for triethyl amine;
TFA for trifluoroacetic acid;
THF for tetrahydrofuran;
TLC for thin layer chromatography;
tBOC or Boc for tert-butyloxy carbonyl;

EXAMPLES

The compounds and processes of the present invention will be better understood in connection with the following illustrative, non-limiting examples Example 1

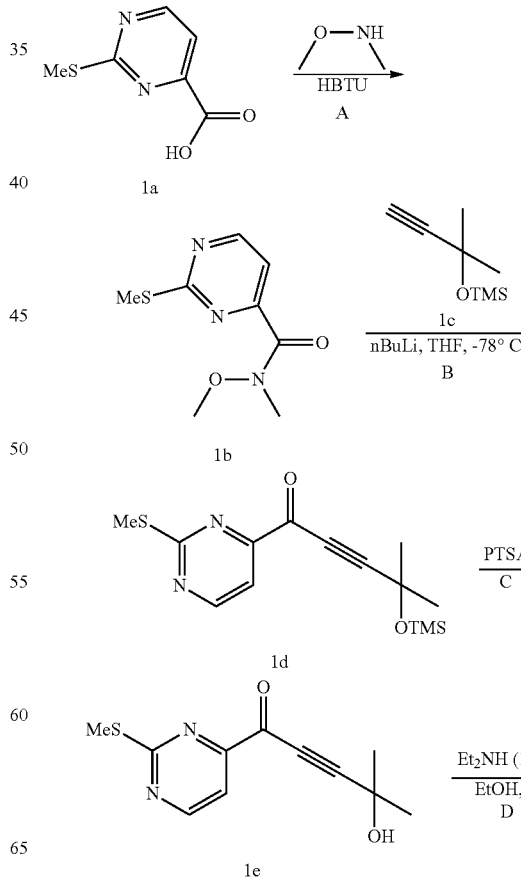

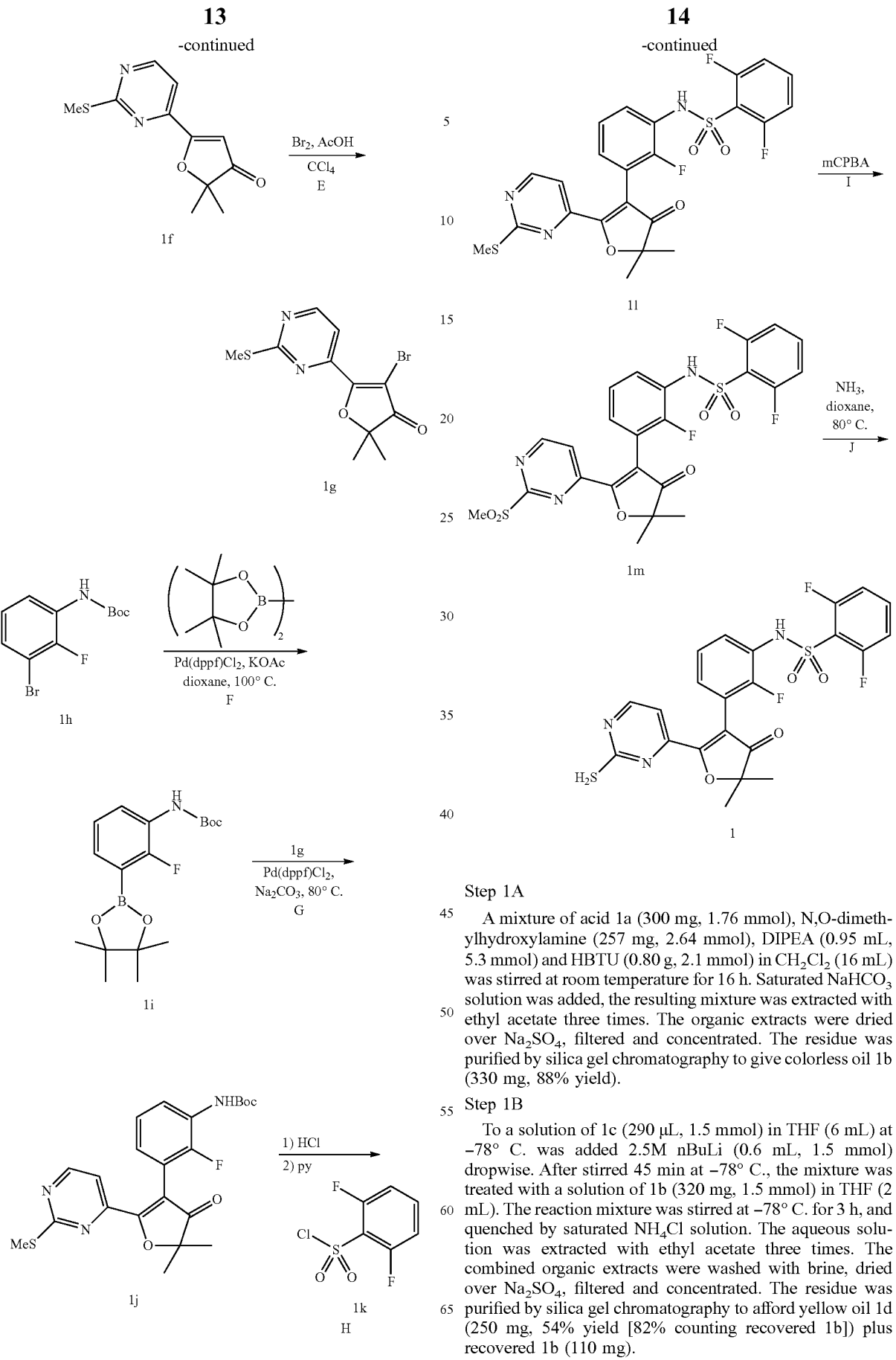

Step 1A

A mixture of acid 1a (300 mg, 1.76 mmol), N,O-dimethylhydroxylamine (257 mg, 2.64 mmol), DIPEA (0.95 mL, 5.3 mmol) and HBTU (0.80 g, 2.1 mmol) in $CH_2Cl_2$ (16 mL) was stirred at room temperature for 16 h. Saturated $NaHCO_3$ solution was added, the resulting mixture was extracted with ethyl acetate three times. The organic extracts were dried over $Na_2SO_4$, filtered and concentrated. The residue was purified by silica gel chromatography to give colorless oil 1b (330 mg, 88% yield).

Step 1B

To a solution of 1c (290 μL, 1.5 mmol) in THF (6 mL) at −78° C. was added 2.5M nBuLi (0.6 mL, 1.5 mmol) dropwise. After stirred 45 min at −78° C., the mixture was treated with a solution of 1b (320 mg, 1.5 mmol) in THF (2 mL). The reaction mixture was stirred at −78° C. for 3 h, and quenched by saturated $NH_4Cl$ solution. The aqueous solution was extracted with ethyl acetate three times. The combined organic extracts were washed with brine, dried over $Na_2SO_4$, filtered and concentrated. The residue was purified by silica gel chromatography to afford yellow oil 1d (250 mg, 54% yield [82% counting recovered 1b]) plus recovered 1b (110 mg).

Step 1C

A mixture of p-toluenesulfonic acid monohydrate (200 mg, 1.05 mmol) and 1d (250 mg, 0.81 mmol) in CH$_2$Cl$_2$ (8 mL) was stirred for 45 min at room temperature. The solution was diluted with CH$_2$Cl$_2$ and washed with water, saturated NaHCO$_3$ solution and water. The organic fraction was dried over Na$_2$SO$_4$, filtered and concentrated. The residue was purified by silica gel chromatography to afford light brown oil 1e (165 mg, 86% yield).

Step 1D

Et$_2$NH (0.11 mL, 1.06 mmol) was added dropwise to a solution of 1c (0.25 g, 1.06 mmol) in EtOH (6 mL). The resulting mixture was stirred at room temperature for 2 h. EtOH was removed on rotovapor, and the residue was dissolved with EtOAc. The organic layer was washed with water, brine, dried over Na$_2$SO$_4$, filtered and concentrated. The residue was purified by silica gel chromatography to give desired product 1f (0.13 g, 52% yield).

Step 1E

To a solution of 1f (100 mg) in CCl$_4$ (10 ml) in ice bath were added AcOH (0.2 ml) and bromine (0.1 mL). The reaction mixture was stirred for 2 h at 0-20° C. Na$_2$S$_2$O$_5$ solution was added, and the resulting mixture was extracted with CH$_2$Cl$_2$ three times. The organic extracts were dried over Na$_2$SO$_4$, filtered and concentrated. The residue was purified by silica gel chromatography to give desired product 1g (96 mg, 72% yield) MS (ESI): m/z=315[M+H]$^+$ Step 1F A mixture of 1h (330 mg, 1.14 mmol), bis(pinacolato)diboron (450 mg), KOAc (330 mg), and Pd(dppf)Cl$_2$ (70 mg) in 1,4-dioxane (6 ml) was stirred in a seal tube under N$_2$ at 100° C. for 18 h. The reaction mixture was filtered through celite, and washed with EtOAc. The filtrate was concentrated and purified by silica gel chromatography to give desired product 1i (320 mg, 82% yield).

Step 1G

A mixture of 1g (25 mg), 1i (32 mg), Na$_2$CO$_3$ (2M, 0.12 mL), and Pd(dppf)Cl$_2$ (13 mg) in 1,4-dioxane(0.8 ml) was stirred in under N$_2$ at 80° C. for 2 h. Water was added, and the mixture was extracted with EtOAc. The organic extracts were washed with brine, dried over Na$_2$SO$_4$, filtered and concentrated. The residue was purified by silica gel chromatography to give yellow oil 1j (35 mg). MS (ESI): m/z=446 [M+H]$^+$.

Step 1H

A mixture of 1j (35 mg) and 4M HCl in dioxane (1 mL) was stirred at room temperature for 2 h. Solvents were removed, and the residue was dissolved in CH$_2$Cl$_2$. Pyridine (36 μL) and 1k (20 μL) were added. The mixture was stirred overnight. Saturated NaHCO$_3$ solution was added to quench the reaction. The reaction mixture was extracted with CH$_2$Cl$_2$ three times. The organic extracts were dried over Na$_2$SO$_4$, filtered and concentrated. The residue was purified by silica gel chromatography to give yellow oil 1l (27 mg). MS (ESI): m/z=522 [M+H]$^+$.

Step 1I

To a solution of 1l (27 mg) in CH$_2$Cl$_2$ (1 ml) was added mCPBA (17 mg). The reaction mixture was stirred for 2 h at room temperature. Sodium thiosulphate solution (1M) was added to quench the reaction. The mixture was extracted with EtOAc. The organic extracts were washed with brine, dried over Na$_2$SO$_4$, filtered and concentrated. The residue was purified by silica gel chromatography to give desired product 1m (22 mg). MS (ESI): m/z=554 [M+H]$^+$.

Step 1J

A mixture of 1m (9 mg), and NH$_4$OH (0.4 mL) in 1,4-dioxane (1.5 mL) was stirred in a sealed tube for 4 h at 80° C. The reaction mixture was purified by reversed phase preparative HPLC to give title compound 1 (3 mg). MS (ESI): m/z=491 [M+H]$^+$.

Example 2

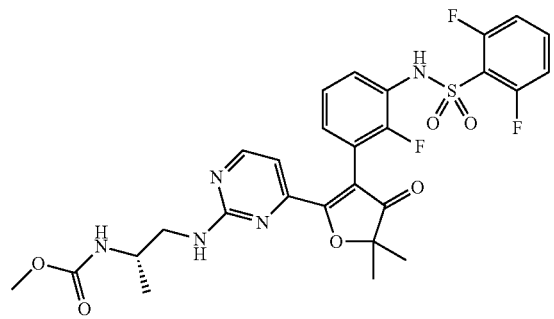

2

A mixture of 1m (13 mg), and (S)-methyl (1-aminopropan-2-yl)carbamate (10 μL, prepared according to the procedures described in WO 2011/25927) in NMP (0.8 mL) was stirred in a sealed vial for 18 h at 90° C. The reaction mixture was purified by reversed phase preparative HPLC to give title compound 2 (4 mg). MS (ESI): m/z=606 [M+H]$^+$.

Example 3

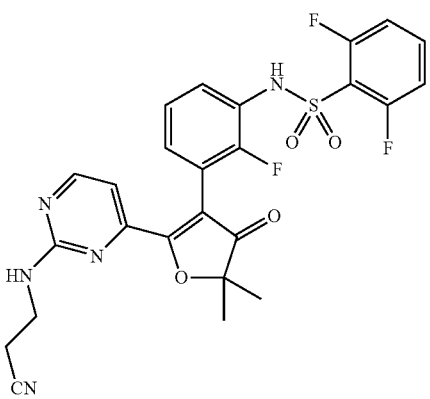

3

Title compound 3 was prepared from 1m and 3-aminopropionitrile using similar procedure as step 1J in example 1. MS (ESI): m/z=544 [M+H]$^+$.

Example 4

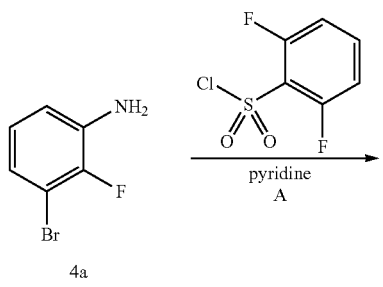

4a

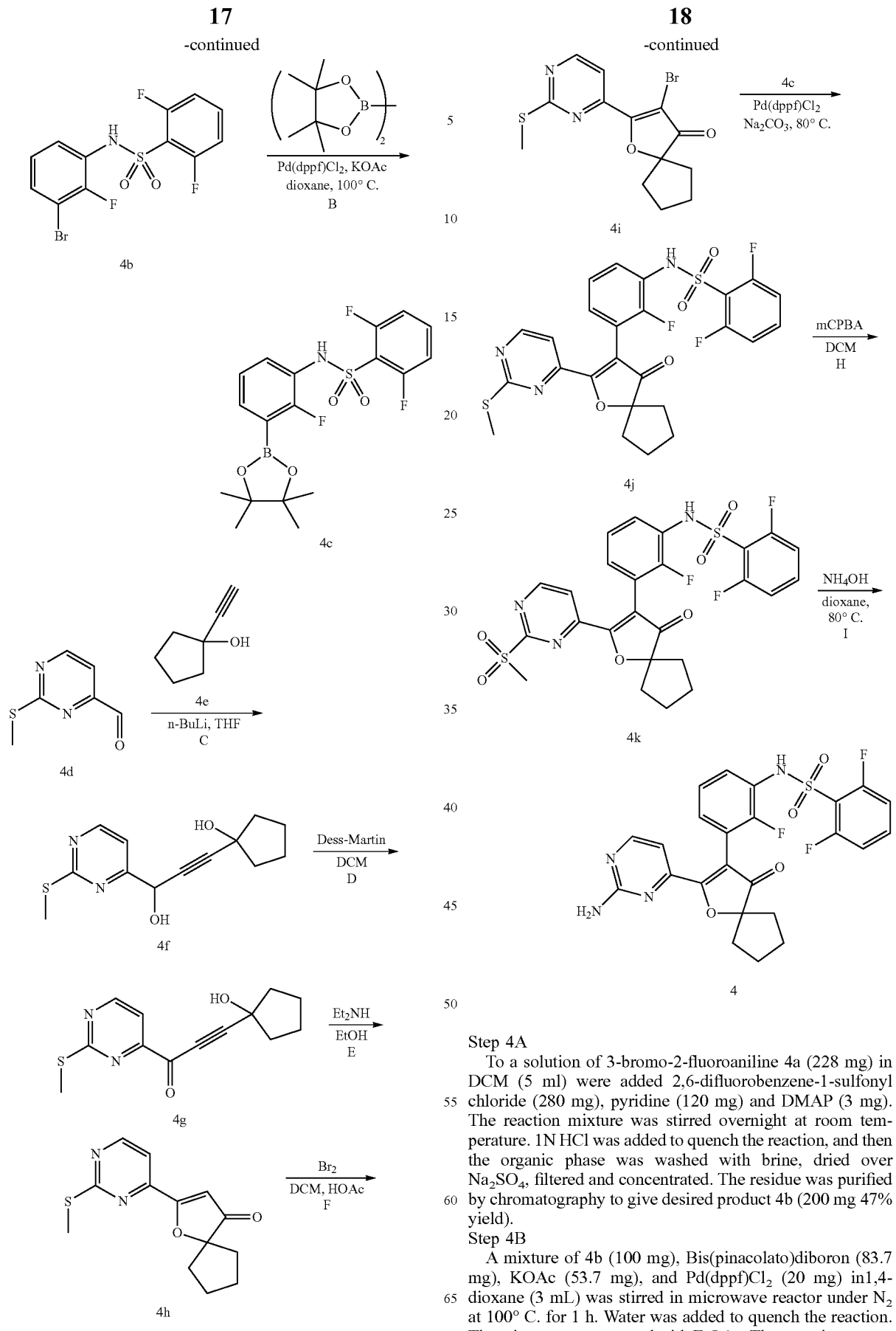

Step 4A

To a solution of 3-bromo-2-fluoroaniline 4a (228 mg) in DCM (5 ml) were added 2,6-difluorobenzene-1-sulfonyl chloride (280 mg), pyridine (120 mg) and DMAP (3 mg). The reaction mixture was stirred overnight at room temperature. 1N HCl was added to quench the reaction, and then the organic phase was washed with brine, dried over $Na_2SO_4$, filtered and concentrated. The residue was purified by chromatography to give desired product 4b (200 mg 47% yield).

Step 4B

A mixture of 4b (100 mg), Bis(pinacolato)diboron (83.7 mg), KOAc (53.7 mg), and $Pd(dppf)Cl_2$ (20 mg) in 1,4-dioxane (3 mL) was stirred in microwave reactor under $N_2$ at 100° C. for 1 h. Water was added to quench the reaction. The mixture was extracted with EtOAc. The organic extracts were washed with brine and dried over Na$_2$SO$_4$, filtered and concentrated. The residue was purified by silica gel chromatography to give desired product 4c (50 mg 39% yield). LC-MS m/z=412[M−H]$^-$.

Step 4C

A solution of 2-(methylthio)pyrimidine-4-carbaldehyde 4d (600 mg, 3.90 mmol) in THF (5 mL) was stirred at −78° C. for 10 min. n-BuLi (8.57 mmol) was added to the mixture at −78° C. The mixture was stirred at −78° C. for 10 min followed by the addition of 1-ethynylcyclopentanol 4e. The mixture was stirred at −78° C. for 30 min. Saturated NH$_4$Cl solution was added to quench the reaction. The reaction mixture was extracted with EtOAc. The organic extracts were washed with brine, and dried over Na$_2$SO$_4$, filtered and concentrated. The residue was purified by chromatography on silica gel to give desired product 4f (363 mg, 37% yield). MS (ESI): m/z=265 [M+H]$^+$ Step 4D To a solution of 4f (363 mg, 30.2 mmol) in DCM (10 ml) in ice bath was added Dess-Martin reagent (644 mg). The reaction mixture was stirred at room temperature for 1 h. It showed the complete conversion of 4f to 4g by LC-MS. Sodium thiosulphate solution (1M) was added to quench the reaction. The reaction mixture was extracted with DCM. The organic extracts were washed with brine, dried over Na$_2$SO$_4$, filtered and concentrated. The residue was purified by chromatography on silica gel to give desired product 4g (261 mg, 73% yield). MS (ESI): m/z=263[M+H]$^+$ Step 4E To a solution of 4g (261 mg, 0.996 mmol) in EtOH (5 ml) was added Et$_2$NH(77 mg) at room temperature. The reaction mixture was stirred over night at room temperature. After the complete conversion of 4g to 4h, the mixture was quenched with water, and then was extracted with EtOAc. The organic extracts were washed with brine, dried over Na$_2$SO$_4$, filtered and concentrated. The residue was purified by chromatography on silica gel to give desired product 4h (160 mg 61% yield). MS (ESI): m/z=263[M+H]$^+$ Step 4F To a solution of 4h (160 mg, 0.613 mmol) in DCM (5 ml) in ice bath were added AcOH (0.2 ml) and bromine (102 mg). The reaction mixture was stirred for 2 h at 0-5° C. Saturated NaHCO$_3$ solution was added to quench the reaction. The organic extracts were washed with brine, dried over Na$_2$SO$_4$, filtered and concentrated. The residue was purified by chromatography to give desired product 4i (180 mg 86% yield) MS (ESI): m/z=341[M+H]$^+$ Step 4G A mixture of 4i (10 mg), 4c (14.5 mg), Na$_2$CO$_3$ (5.6 mg), Pd(dppf)Cl$_2$ (2.1 mg) and water (1 mL) in 1.4-dioxane(4 ml) was stirred in microwave under N$_2$ at 100° C. for 45 min. Water was added to quench the reaction. The mixture was extracted with EtOAc. The organic extracts were washed with brine, dried over Na$_2$SO$_4$, filtered and concentrated. The residue was purified by silica gel chromatography to give yellow product 4j (12 mg 39% yield). LC-MS m/z=548 [M+H]$^+$ Step 4H To a solution of 4j (12 mg) in DCM (2 ml) were added mCPBA(13 mg). The reaction mixture was stirred for 2 h at room temperature. Sodium thiosulphate solution (1M) was added to quench the reaction. The mixture was extracted with DCM. The organic extracts were washed with brine, dried over Na$_2$SO$_4$, filtered and concentrated. The residue was purified by silica gel chromatography to give desired product 4k (12 mg 95% yield).

Step 4I

A mixture of 4k (12 mg) and NH$_4$OH (2 ml) in 1,4-dioxane was stirred for 12 h at 90° C. Water and EtOAc were added to the mixture. The organic phase was washed with brine, dried over Na$_2$SO$_4$, filtered and concentrated. The residue was purified by reversed phase preparative HPLC to give title compound 4 (4 mg). MS (ESI): m/z=517 [M+H]$^+$.

Examples 5 to 10 (Table 1) were made from 3,5-dimethylhex-1-yn-3-ol and corresponding amine via the similar conditions described in steps 1A~1J of Example 1.

TABLE 1

Compounds of formula:

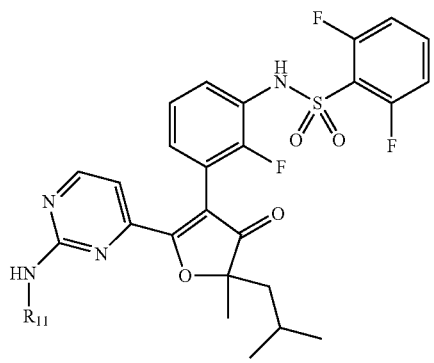

| Example No. | R$_{11}$ | MS(ESI) m/z [M + H] |
|---|---|---|
| 5 | H | 533 |
| 6 | ~~~CH$_2$CH$_2$CN | 586 |
| 7 | ~~~CH(iPr)NHC(O)OCH$_3$ | 648 |
| 8 | ~~~CH$_2$-thiazol-2-yl | 630 |
| 9 | ~~~CH$_2$-(pyrrolidin-2-yl) | 616 |
| 10 | ~~~CH$_2$-(tetrahydrofuran-2-yl) | 617 |

Example 11

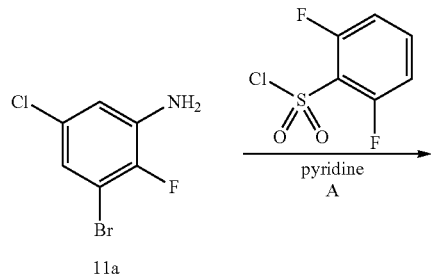

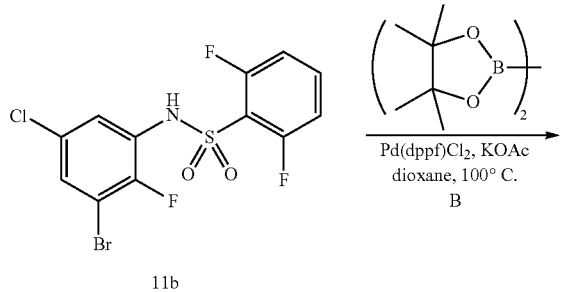

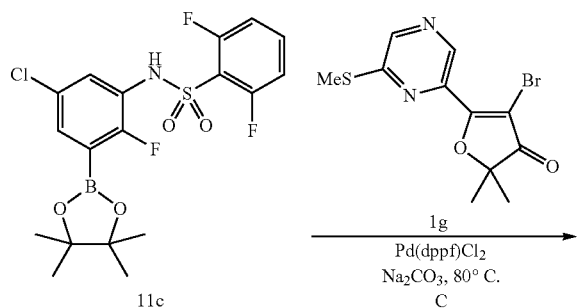

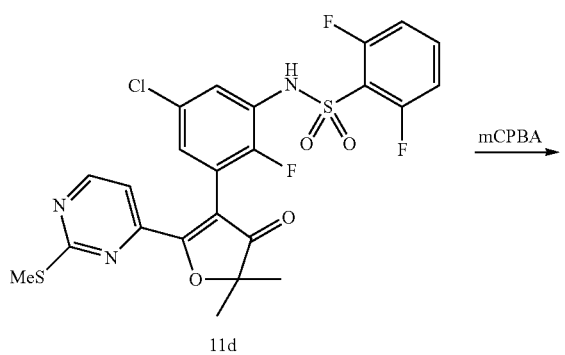

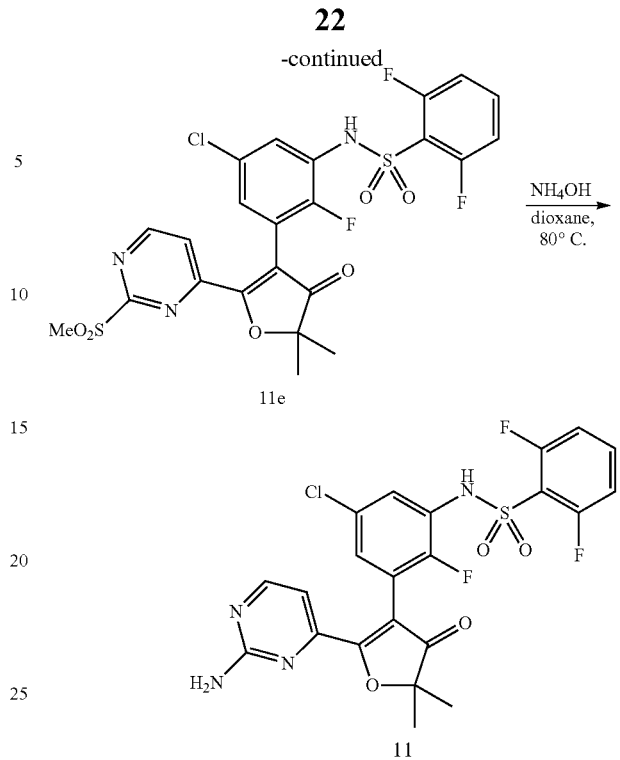

Step 11A
To a solution of 11a (212 mg, 0.81 mmol) and pyridine (0.16 mL) in DCM (3 ml) was added 2,6-difluorobenzene-1-sulfonyl chloride (132 mg, 0.97 mmol). The reaction mixture was stirred overnight at room temperature. The mixture was treated with water and extracted with EtOAc. The organic extracts were washed with brine, dried over $Na_2SO_4$, filtered and concentrated. The residue was purified by silica gel chromatography to give desired product 11b (290 mg).

Step 11B
A mixture of the intermediate 11b (180 mg), bis(pinacolato)diboron (170 mg), KOAc (130 mg), and Pd(dppf)Cl$_2$ (36 mg) in 1,4-dioxane (8 mL) was stirred in a sealed tube under N$_2$ at 100° C. for 18 h. Water was added to quench the reaction. The reaction mixture was filtered through Celite® and washed with EtOAc. The filtrate was concentrated and purified by silica gel chromatography to give desired product 11c (150 mg, 75% yield).

Step 11C
A mixture of 1g (33 mg), 11c (56 mg), Na$_2$CO$_3$ (2M in water, 0.2 mL), Pd(dppf)Cl$_2$ (8 mg) in 1,4-dioxane(1.5 mL) was stirred under N$_2$ at 80° C. for 18 h. Water was added, the mixture was extracted with EtOAc. The organic extracts were washed with brine, dried over Na$_2$SO$_4$, filtered and concentrated. The residue was purified by silica gel chromatography to give yellow oil 11d (43 mg). MS (ESI): m/z=556 [M+H]$^+$.

Step 11D
To a solution of 11d (43 mg) in DCM (2 ml) were added mCPBA(30 mg). The reaction mixture was stirred for 2 h at room temperature. Solvents were removed. The resulting residue was purified by silica gel chromatography to give desired product 11e (25 mg).

Step 11E
A mixture of 11e (25 mg) and NH$_4$OH (0.2 ml) in 1,4-dioxane (1.5 mL) was stirred for 4 h at 78° C. Solvents were removed. The residue was purified by reversed phase preparative HPLC to give title compound 11 (20 mg). MS (ESI): m/z=525 [M+H]$^+$.

Example 12

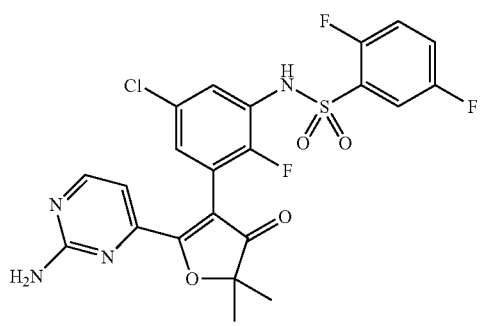

The above compound was made from 11a and 2,5-difluorobenzene-1-sulfonyl chloride using similar procedures described in example 11. MS (ESI): m/z=525 [M+H]+.

Example 13

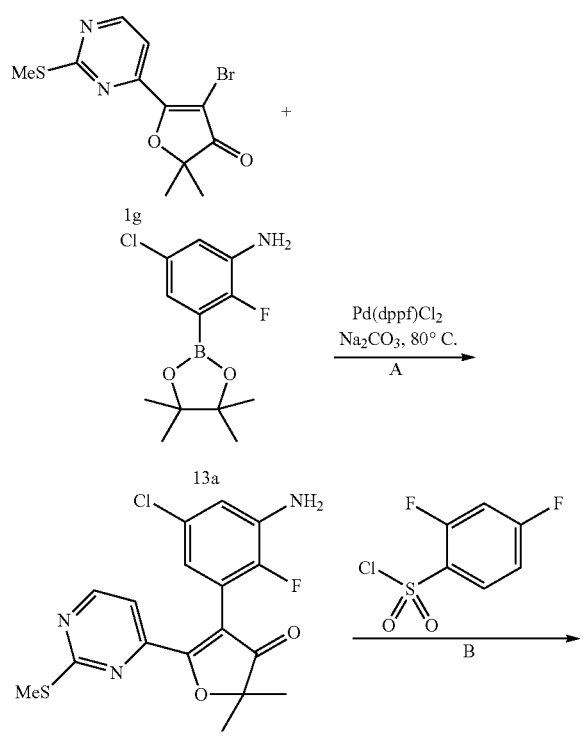

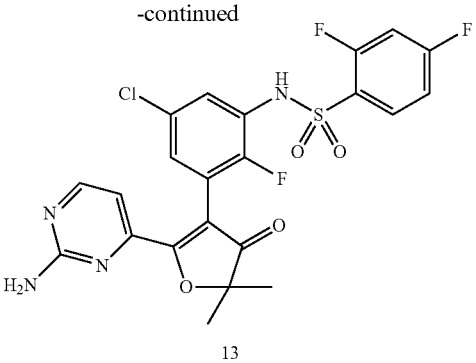

Step 13A

A mixture of 1g (27 mg), 13a (28 mg), Na$_2$CO$_3$ (2M in water, 0.15 mL), Pd(dppf)Cl$_2$ (25 mg) in 1,4-dioxane (1.5 mL) was stirred under N$_2$ at 80° C. for 3 h. Water was added, and the mixture was extracted with EtOAc. The organic extracts were washed with brine, dried over Na$_2$SO$_4$, filtered and concentrated. The residue was purified by silica gel chromatography to give 13b (15 mg). MS (ESI): m/z=380 [M+H]+.

Step 13B

A mixture of 13b (7 mg), pyridine (20 μL) and 2,4-difluorobenzene-1-sulfonyl chloride (12 μL) in DCM (0.7 mL) was stirred at rt for 18 h. Solvents were removed by evaporation. The resulting residue was purified by silica gel chromatography to give desired product 13c (7 mg). MS (ESI): m/z=556 [M+H]+.

Step 13C

To a solution of 13c (7 mg) in CH$_2$Cl$_2$ (1 ml) was added mCPBA (8 mg). The reaction mixture was stirred for 3 h at room temperature. Solvents were removed by evaporation. The resulting residue was purified by silica gel chromatography to give the oxidation product, which was stirred with NH$_4$OH (0.1 mL) and 1,4-dioxane (0.8 mL) in a closed vial for 2 h at 80° C. The reaction mixture was purified by silica gel chromatography to give title compound 13 (4.8 mg). MS (ESI): m/z=525 [M+H]+.

Example 14

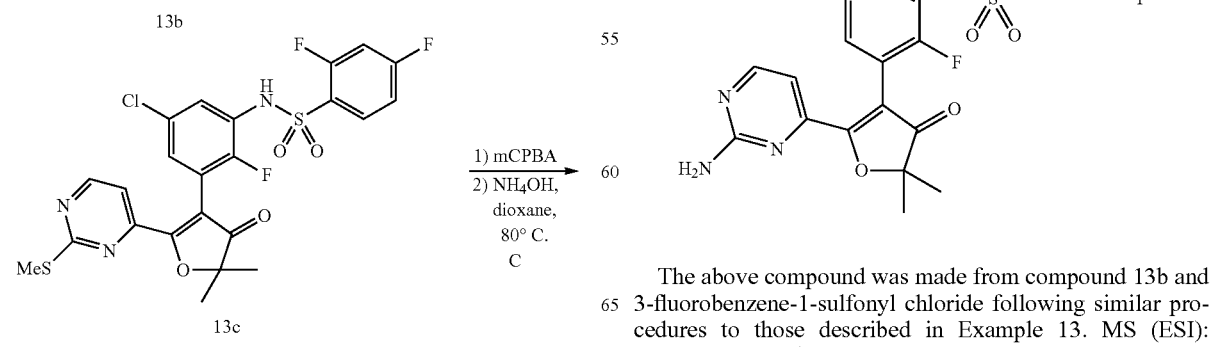

The above compound was made from compound 13b and 3-fluorobenzene-1-sulfonyl chloride following similar procedures to those described in Example 13. MS (ESI): m/z=507 [M+H]+.

Example 15

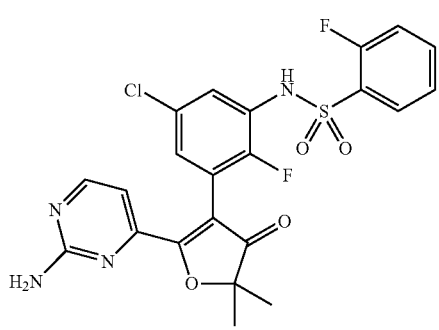

The above compound was made from compound 13b and 2-fluorobenzene-1-sulfonyl chloride following similar procedures to those described in Example 13. MS (ESI): m/z=507 [M+H]⁺.

Example 16

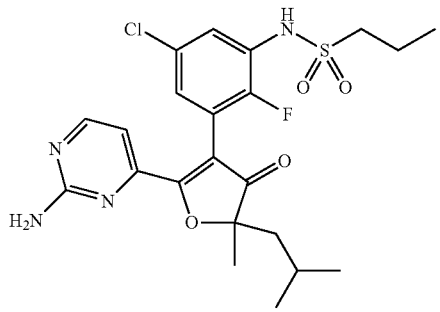

The above compound was made by using similar procedures to those described in Examples 1 and 11. MS (ESI): m/z=497 [M+H]⁺.

Example 17

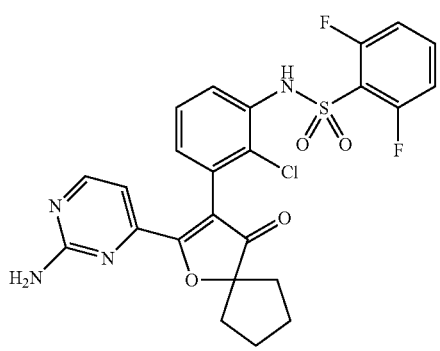

The above compound was made from compound 4i and 3-bromo-2-chloroaniline following similar procedures to those described in Example 4. MS (ESI): m/z=533 [M+H]⁺.

Example 18

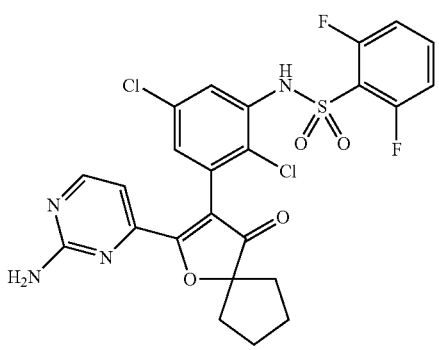

The above compound was made from compound 4i and 2,5-dichloroaniline following similar procedures to those described in Example 4. MS (ESI): m/z=567 [M+H]⁺.

Examples 19 to 29 (Table 2) were prepared by using similar procedures described to those described in Examples 1, 4 and 11.

TABLE 2

Compounds of formula:

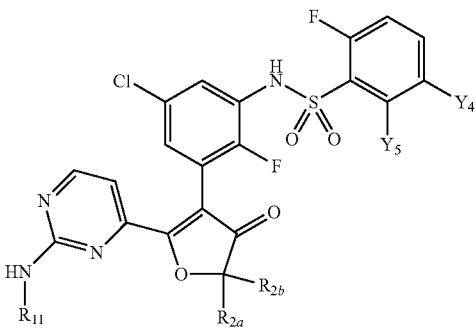

| Example No. | $R_{2a}$ | $R_{2b}$ | $Y_4$ | $Y_5$ | $R_{11}$ | MS(ESI) m/z [M + H]⁺ |
|---|---|---|---|---|---|---|
| 19 | Me | iBu | H | F | H | 567 |
| 20 | Me | iBu | H | F | ⸻CN | 620 |
| 21 | Me | Me | H | F | ⸻CN | 578 |
| 22 | Me | Me | F | H | MeO-C(O)-NH- | 640 |
| 23 | Me | Me | F | H | ⸻CN | 578 |

TABLE 2-continued

Compounds of formula:

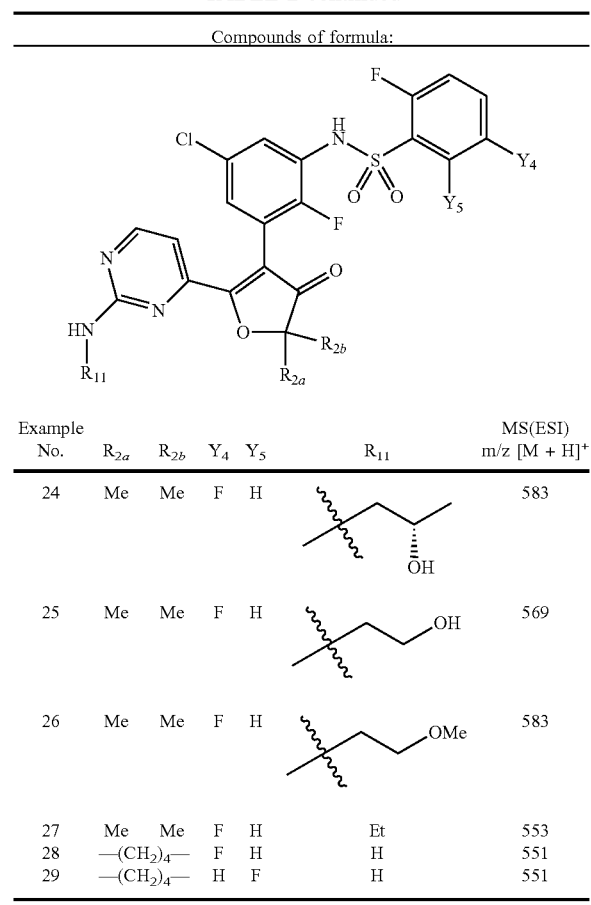

| Example No. | $R_{2a}$ | $R_{2b}$ | $Y_4$ | $Y_5$ | $R_{11}$ | MS(ESI) m/z $[M + H]^+$ |
|---|---|---|---|---|---|---|
| 24 | Me | Me | F | H | ⟨CH(CH₃)CH(OH)CH₃⟩ | 583 |
| 25 | Me | Me | F | H | ⟨CH₂CH₂OH⟩ | 569 |
| 26 | Me | Me | F | H | ⟨CH₂CH₂OMe⟩ | 583 |
| 27 | Me | Me | F | H | Et | 553 |
| 28 | —(CH₂)₄— | | F | H | H | 551 |
| 29 | —(CH₂)₄— | | H | F | H | 551 |

BIOLOGICAL ASSAYS $BRAF^{V600E}$ enzymatic activity assay: The $BRAF^{V600E}$ enzymatic assay was performed using a LanthaScreen kinase assay kit purchased from Life Technologies (Grand Island, N.Y.). The assay was conducted according to the procedure provided in the assay kit. In brief, the enzyme reaction was carried out in the kinase reaction buffer containing $BRAF^{V600E}$ (20 ng/mL), ATP (2 µM), Fluorescein-MAP2K1 inactive substrate (0.4 µM), HEPES (50 mM, pH 7.5), 0.01% BRIJ-35, $MgCl_2$ (10 mM), and EGTA (1 mM) in the presence or absence of the tested compounds at various concentrations in a 384-well plate at room temperature (22±1° C.) for 60 minutes. The final reaction volume for each reaction was 10 µl. The reaction was stopped by addition of 10 µl of TR-FRET dilution buffer kinase supplemented with kinase quench buffer (10 mM final) and Tb-anti-pMAP2K1 (2 nM final). The plate was further incubated at room temperature for another 60 minutes, and the fluorescent signals were read on Victor 5 (Perkin Elmer) with excitation at 340 nM and emission at 495 and 520 nM. The assay signal was determined as a ratio of FRET-specific signal measured with emission filter at 520 nM to that of the signal measured with Tb-specific emission filter at 495 nM. $IC_{50}$ value was calculated using appropriate programs in GraphPad Prism by plotting the logarithm of the concentration versus percent inhibition. The $IC_{50}$ values for the example compounds are shown in Table 3.

Cell proliferation assay: A375, Colo-205, Calu-6, and SW-480 cells were purchased from American Type Culture Collection (USA). All cells were cultured in the recommended medium and serum concentration. Cells were maintained at 37° C. in a humidified atmosphere with 5% $CO_2$. For cell proliferation assay, cells were seeded in 96-well pates at a density of 1,000 to 5,000 cells per well and cultured overnight at 37° C. in a medium supplemented with 5-10% FBS. On the next day, the test articles at various concentrations or vehicle control (1% DMSO) were added into cell culture. After 3-day treatment, the growth of cells was assayed by the CellTiter-Glo® Luminestceaent Cell Viability Assay (Promega). $IC_{50}$ value was calculated using GraphPad Prism by plotting the logarithm of the concentration versus percent inhibition of cell growth. The $IC_{50}$ value for the example compounds is shown in Table 3.

TABLE 3

Biological Testing Results

| Example No. | $BRAF^{V600E}$ Lantha $IC_{50}$ (µM) | A375 cell growth $IC_{50}$ (µM) |
|---|---|---|
| 1 | 0.16 | 0.97 |
| 2 | 0.097 | 0.63 |
| 3 | 0.013 | 0.47 |
| 4 | 0.029 | 0.51 |
| 5 | 0.092 | 2.3 |
| 6 | 0.0096 | 12.0 |
| 7 | 0.027 | 0.87 |
| 8 | 0.26 | 27 |
| 9 | 2 | — |
| 10 | 0.75 | — |
| 11 | 0.0055 | 0.018 |
| 12 | 0.0006 | 0.0014 |
| 13 | 0.010 | 0.35 |
| 14 | 0.0012 | 0.12 |
| 15 | 0.0025 | 0.11 |
| 16 | 0.07 | 0.25 |
| 17 | 0.0037 | 0.15 |
| 18 | 0.0024 | 0.007 |
| 19 | 0.027 | 0.041 |
| 20 | 0.029 | 0.16 |
| 21 | 0.0025 | 0.20 |
| 22 | 0.050 | 0.18 |
| 23 | 0.013 | 0.051 |
| 24 | 0.024 | 0.41 |
| 25 | 0.011 | 0.16 |
| 26 | 0.050 | 0.26 |
| 27 | 0.0028 | 0.32 |
| 28 | 0.0026 | 0.011 |
| 29 | 0.0013 | 0.018 |

The foregoing preferred embodiments and examples are provided for illustration only and are not intended to limit the scope of the invention. Various changes and modifications to the disclosed embodiments will be apparent to those skilled in the art based on the present disclosure, and such changes and modifications, including, without limitation, those relating to the chemical structures, substituents, derivatives, formulations and/or methods of preparation, may be made without departure from the spirit and scope of the present invention.

The invention claimed is:

1. A compound of formula (I):

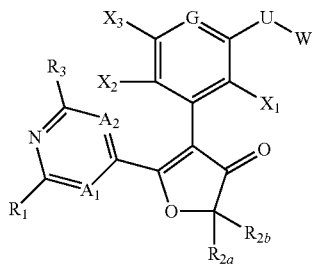

or a pharmaceutically acceptable salt or solvate thereof, wherein:
- $A_1$ and $A_2$ are independently CH or N;
- G is N or $CX_4$;
- $R_1$ is selected from the group consisting of hydrogen, halogen, $-NR_{11}R_{14}$, $-OR_{12}$, or $-S(O)_{0-2}R_{13}$;
- $R_{11}$ is selected from the group consisting of hydrogen, alkyl, alkenyl, alkynyl, cycloalkyl, cycloalkenyl, heterocyclyl, aryl, and heteroaryl, each group except hydrogen optionally substituted;
- $R_{12}$, $R_{13}$, and $R_{14}$ are independently selected from the group consisting of hydrogen, alkyl and cycloalkyl;
- $R_{2a}$ and $R_{2b}$ are independently selected from the group consisting of hydrogen, alkyl, alkenyl, alkynyl, cycloalkyl, cycloalkenyl, heterocyclyl, aryl, and heteroaryl; or alternatively $R_{2a}$ and $R_{2b}$ together with the carbon atom to which they are attached form a cyclic moiety selected from the group consisting of cycloalkyl, cycloalkenyl, and heterocyclyl, each optionally substituted;
- $R_3$ is selected from the group consisting of hydrogen, halogen, hydroxyl, alkyl, alkoxy, and $NR_{31}R_{32}$;
- $R_{31}$ and $R_{32}$ are independently hydrogen or alkyl;
- $X_1$ through $X_4$ are independently selected from the group consisting of hydrogen, halogen, cyano, nitro, hydroxyl, alkyl, alkoxy, and amino;
- U is selected from the group consisting of $-NH-$, $-NHC(O)-$, $-NHS(O)_n-$, $-NHC(O)O-$, $-NHC(O)NH-$, $-O-$, $-C(O)-$, $-C(O)O-$, $-OC(O)NH-$, $-C(O)NH-$, $-S-$, $-SO_2-$, and $-S(O)_nNH-$, wherein each n is independently 1 or 2; and
- W is selected from the group consisting of alkyl, alkenyl, alkynyl, cycloalkyl, cycloalkenyl, heterocyclyl, aryl, and heteroaryl, each optionally substituted.

2. The compound of claim 1, wherein $A_1$ is CH, and $A_2$ is CH or N.

3. The compound of claim 1, wherein $A_1$ is N, and $A_2$ is N.

4. The compound of claim 1, wherein $A_1$ is N, and $A_2$ is CH, characterized by formula (II):

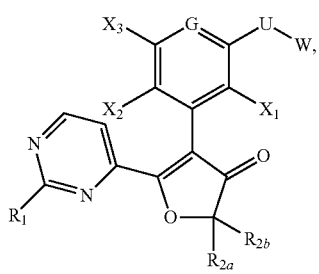

or a pharmaceutically acceptable salt or solvate thereof.

5. The compound of claim 1, or a pharmaceutically acceptable salt or solvate thereof, wherein G is nitrogen (N).

6. The compound of claim 1, or a pharmaceutically acceptable salt or solvate thereof, wherein G is $CX_4$.

7. The compound of claim 1, wherein U is $-NHS(O)_2-$ or $-S(O)_nNH-$.

8. The compound of claim 1, wherein W is alkyl optionally substituted by 1 to 3 substituents independently selected from the group consisting of hydroxyl, halogen, cyano, and alkoxy; or aryl optionally substituted by 1 to 5 substituents independently selected from the group consisting of halogen, alkyl, alkoxy, haloalkyl, haloalkoxy, hydroxy, cyano, nitro, and amino.

9. The compound of claim 1, wherein $R_1$ is $-NR_{11}R_{14}$.

10. The compound of claim 9, wherein $R_{14}$ is hydrogen, characterized by formula (III):

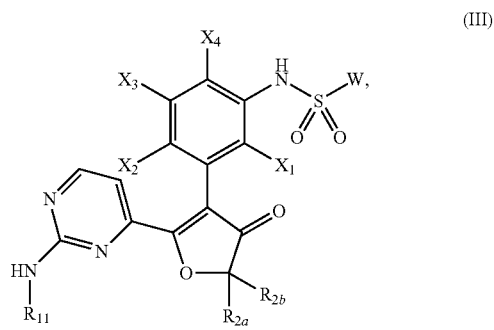

or a pharmaceutically acceptable salt or solvate thereof.

11. The compound of claim 10, or a pharmaceutically acceptable salt or solvate thereof, wherein:
- $R_{11}$ is hydrogen or alkyl optionally substituted by 1 to 3 groups independently selected from the group consisting of aryl, heteroaryl, cyano, cycloalkyl, heterocyclyl, halogen, hydroxyl, $-NR_{15}R_{16}$, $-OR_{17}$, and $-S(O)_{0-2}R_{18}$;
- $R_{15}$ is hydrogen, optionally substituted alkyl, $C(O)R_{19}$, or $-C(O)OR_{19}$;
- $R_{16}$ is hydrogen or optionally substituted alkyl;
- $R_{17}$ is alkyl, $-C(O)R_{20}$, or $-C(O)NHR_{20}$;
- $R_{18}$ is alkyl, alkoxy, halogen, or hydroxyl;
- $R_{19}$ is optionally substituted alkyl;
- $R_{20}$ is hydrogen or optionally substituted alkyl; and
- W is $C_6$-$C_{10}$ aryl optionally substituted by 1 to 5 substituents independently selected from the group consisting of halogen, $C_1$-$C_6$ alkyl, $C_1$-$C_6$ alkoxy, $C_1$-$C_6$ haloalkyl, $C_1$-$C_6$ haloalkoxy, hydroxy, cyano, nitro, and amino.

12. The compound of claim 11, wherein W is optionally substituted phenyl, characterized by formula (IV):

(IV)

[Structure of formula IV showing a sulfonamide-linked biaryl with furanone and aminopyrimidine substituents, with variables Y1-Y5, X1-X4, R11, R2a, R2b]

or a pharmaceutically acceptable salt or solvate thereof, wherein:

$Y_1$ through $Y_5$ are independently selected from the group consisting of hydrogen, halogen, cyano, nitro, hydroxyl, alkyl, alkoxy, and amino.

13. The compound of claim 12, or a pharmaceutically acceptable salt or solvate thereof, wherein $Y_1$, $Y_2$, $Y_3$, $Y_4$ and $Y_5$ are independently hydrogen or halogen.

14. The compound of claim 12, or a pharmaceutically acceptable salt or solvate thereof, wherein one, two or three of $Y_1$, $Y_2$, $Y_3$, $Y_4$ and $Y_5$ are halogen and the rest are hydrogen.

15. The compound of claim 14, or a pharmaceutically acceptable salt or solvate thereof, wherein one or two of $Y_1$, $Y_2$, $Y_3$, $Y_4$ and $Y_5$ are halogen and the rest are hydrogen.

16. The compound of claim 14, or a pharmaceutically acceptable salt or solvate thereof, wherein any said halogen is fluorine (F) or chlorine (Cl).

17. The compound of claim 16, or a pharmaceutically acceptable salt or solvate thereof, wherein said halogen is fluorine (F).

18. The compound of claim 14, or a pharmaceutically acceptable salt or solvate thereof, wherein $X_1$ through $X_4$ are independently hydrogen or halogen.

19. The compound of claim 18, or a pharmaceutically acceptable salt or solvate thereof, wherein $X_2$ and $X_4$ are hydrogen.

20. The compound of claim 19, or a pharmaceutically acceptable salt or solvate thereof, wherein $X_1$ and $X_3$ are independently hydrogen, fluorine (F) or chlorine (Cl).

21. The compound of claim 20, or a pharmaceutically acceptable salt or solvate thereof, wherein $R_{11}$ is hydrogen or $C_1$-$C_6$ alkyl optionally substituted by 1 to 3 groups independently selected from the group consisting of $C_6$-$C_{10}$ aryl, 5- to 10-membered heteroaryl, $C_3$-$C_8$ cycloalkyl, 5- to 10-membered heterocyclyl, halogen, cyano, hydroxyl, —$NR_{15}R_{16}$, —$OR_{17}$, and —$S(O)_2R_{18}$;

$R_{15}$ is hydrogen, $C_1$-$C_4$ alkyl, or —$C(O)OR_{19}$;
$R_{16}$ is hydrogen or $C_1$-$C_4$ alkyl;
$R_{17}$ is $C_1$-$C_4$ alkyl, —$C(O)R_{20}$, or —$C(O)NHR_{20}$;
$R_{18}$ is alkyl, alkoxy, halogen, or hydroxyl;
$R_{19}$ is $C_1$-$C_4$ alkyl; and
$R_{20}$ is hydrogen or $C_1$-$C_4$ alkyl.

22. The compound of claim 21, or a pharmaceutically acceptable salt or solvate thereof, wherein $R_{2a}$ and $R_{2b}$ are independently selected from the group consisting of hydrogen, and optionally substituted alkyl, alkenyl, alkynyl, cycloalkyl, cycloalkenyl, heterocyclyl, aryl, and heteroaryl.

23. The compound of claim 22, wherein $R_{2a}$ and $R_{2b}$ are independently $C_1$-$C_6$ alkyl.

24. The compound of claim 21, or a pharmaceutically acceptable salt or solvate thereof, wherein $R_{2a}$ and $R_{2b}$ together with the carbon atom to which they are attached form a cyclic moiety selected from the group consisting of optionally substituted cycloalkyl, cycloalkenyl, and heterocyclyl.

25. The compound of claim 24, or a pharmaceutically acceptable salt or solvate thereof, wherein $R_{2a}$ and $R_{2b}$ together with the carbon atom to which they are attached form a $C_3$-$C_8$ cycloalkyl.

26. The compound of claim 22, or a pharmaceutically acceptable salt or solvate thereof, wherein $R_{11}$ is hydrogen, $C_1$-$C_6$ alkyl,

[Structures of various R11 substituent groups: propylnitrile, methoxyethyl, hydroxy-dimethyl, hydroxypropyl, methyl carbamate alanine, thiazolylmethyl, pyrrolidinylmethyl, tetrahydrofuranylmethyl]

27. The compound of claim 12, or a pharmaceutically acceptable salt or solvate thereof, wherein:

$R_{11}$ is hydrogen, $C_1$-$C_6$ alkyl,

[Structures of various R11 substituent groups: propylnitrile, methoxyethyl, hydroxy-dimethyl, hydroxypropyl, methyl carbamate alanine, thiazolylmethyl, pyrrolidinylmethyl, tetrahydrofuranylmethyl]

$R_{2a}$ and $R_{2b}$ are independently $C_1$-$C_6$ alkyl; or alternatively $R_{2a}$ and $R_{2b}$ together are —$(CH_2CH_2CH_2CH_2)$— or —$(CH_2CH_2CH_2CH_2CH_2)$—;

$X_1$ and $X_3$ are independently hydrogen, fluorine, or chlorine (Cl);

$X_2$ and $X_4$ are hydrogen; and one or two of $Y_1$, $Y_2$, $Y_3$, $Y_4$, and $Y_5$ are fluorine, and the rest are hydrogen.

28. The compound of claim 1, or a pharmaceutically acceptable salt or solvate thereof, selected from the group consisting of:
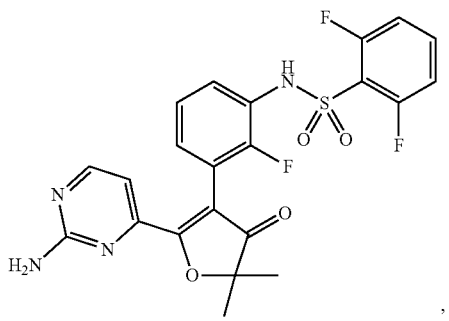
,
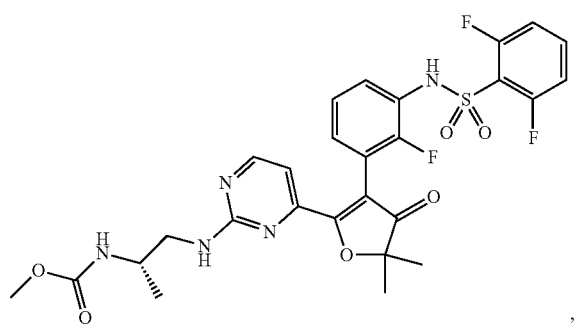
,
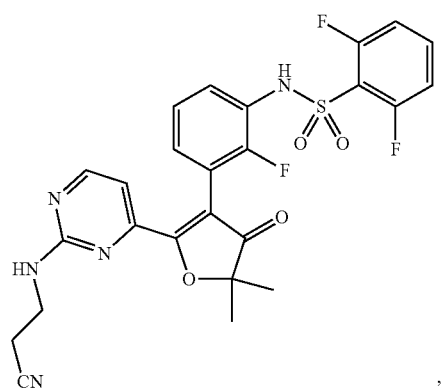
,
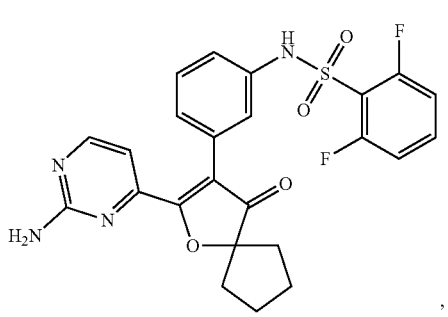
,
-continued
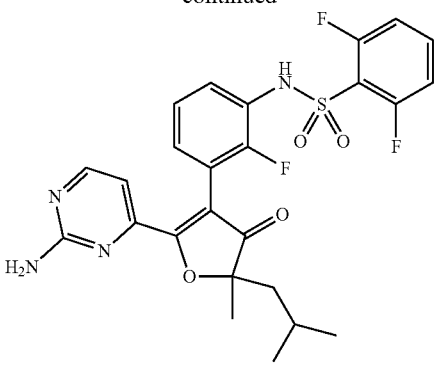
,
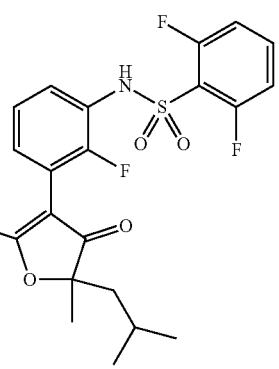
,
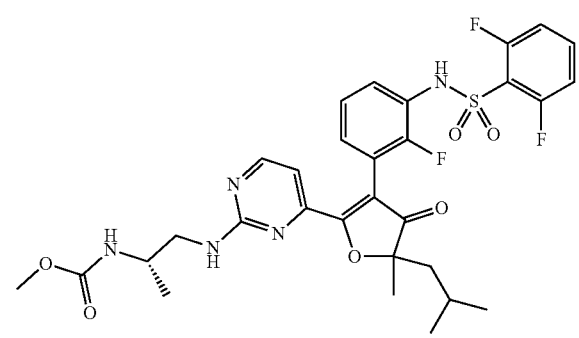
,
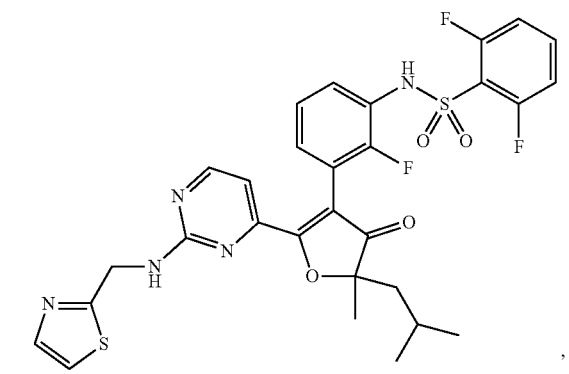
,

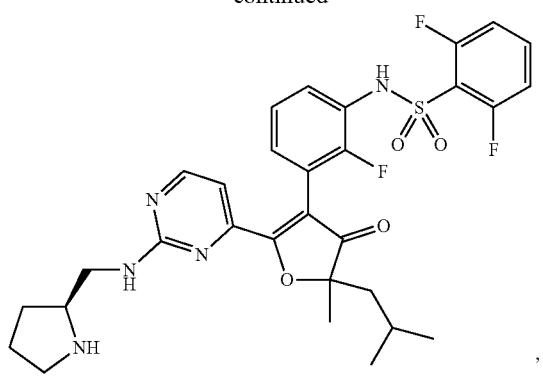
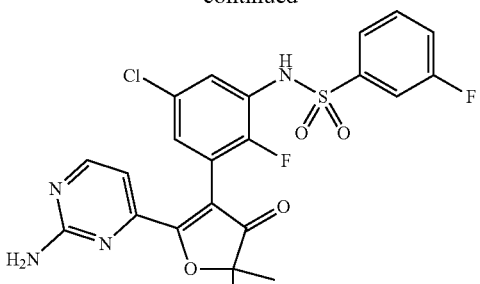
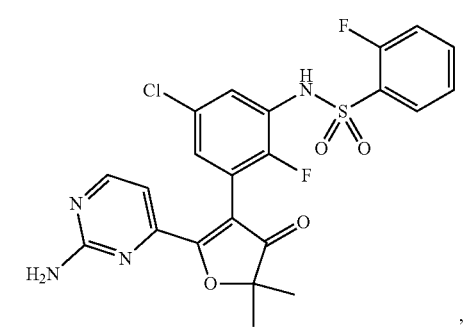
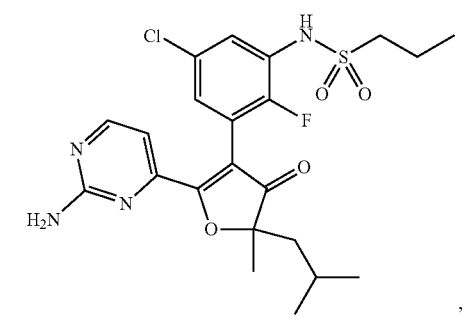
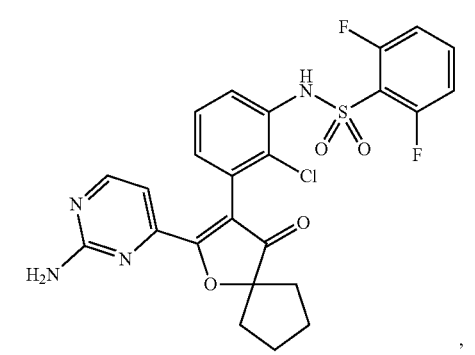
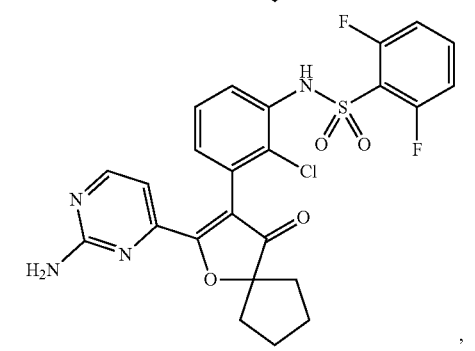

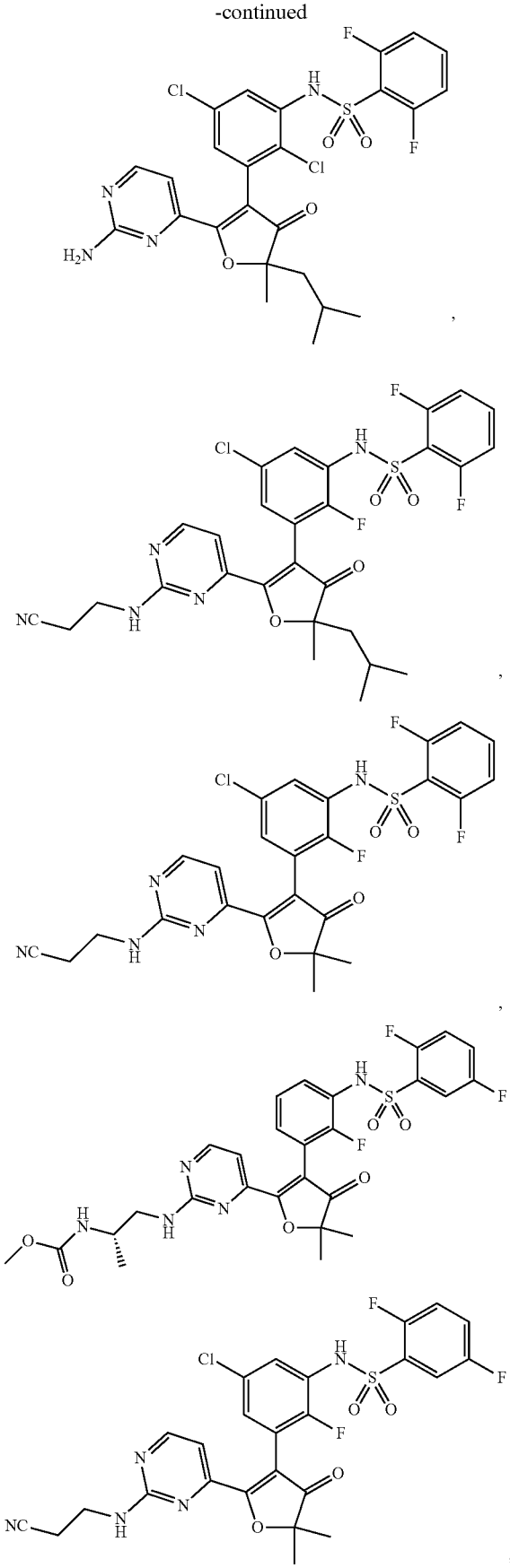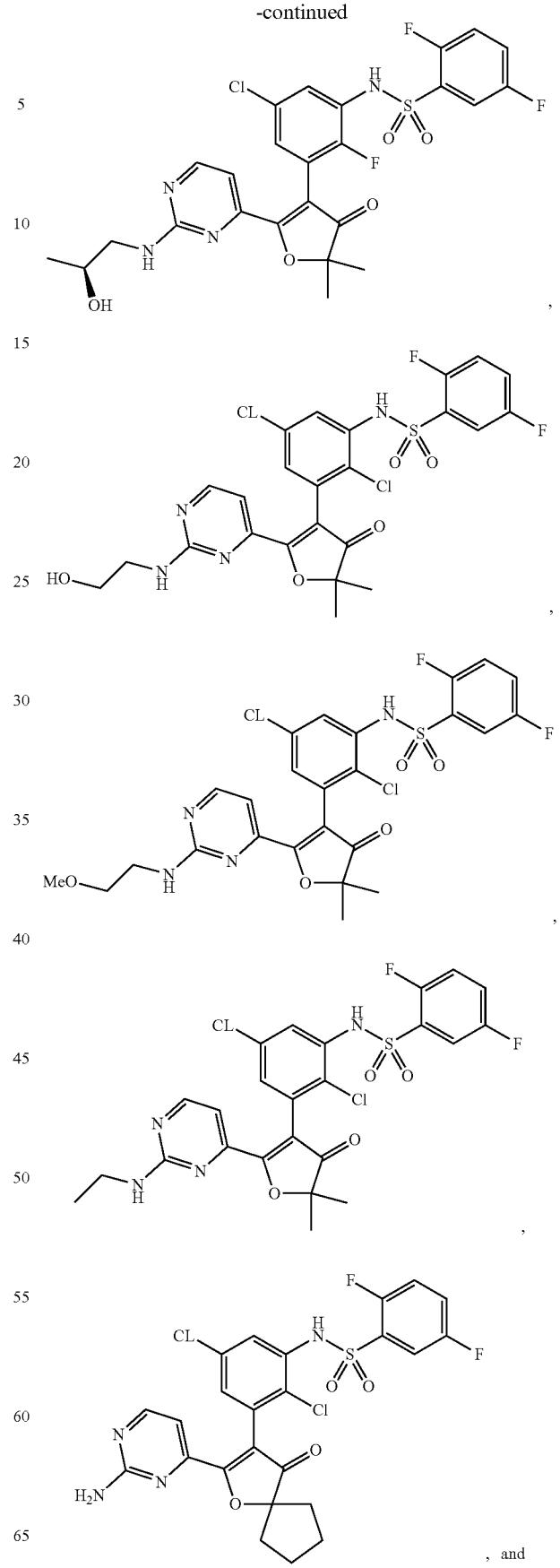

-continued

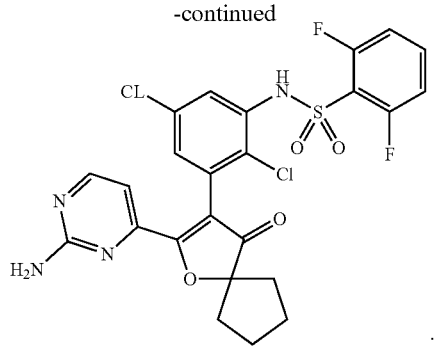

29. A pharmaceutical composition comprising a compound of claim 1, or a pharmaceutically acceptable salt or solvate thereof, and a pharmaceutically acceptable carrier.

30. A method of treating cancer in a subject, comprising administering to the subject a therapeutically effective amount of a compound of claim 1, or a pharmaceutically acceptable salt or solvate thereof.

31. The method of claim 30, wherein the cancer is selected from melanoma; papillary thyroid, colorectal, ovarian, breast, lung or leukemia.

* * * * *